(12) United States Patent
Sri

(10) Patent No.: US 10,548,714 B2
(45) Date of Patent: Feb. 4, 2020

(54) POSTERIOR CHAMBER INTRAOCULAR LENS WITH SWIVEL HAPTICS FOR CAPSULOTOMY FIXATION

(71) Applicant: Ganesh Sri, Bangalore (IN)

(72) Inventor: Ganesh Sri, Bangalore (IN)

( * ) Notice: Subject to any disclaimer, the term of this patent is extended or adjusted under 35 U.S.C. 154(b) by 0 days.

(21) Appl. No.: 15/554,417

(22) PCT Filed: Aug. 5, 2016

(86) PCT No.: PCT/IB2016/054731
§ 371 (c)(1),
(2) Date: Aug. 29, 2017

(87) PCT Pub. No.: WO2017/175043
PCT Pub. Date: Oct. 12, 2017

(65) Prior Publication Data
US 2018/0280133 A1    Oct. 4, 2018

(30) Foreign Application Priority Data

Apr. 5, 2016   (IN) .............................. 201641011936

(51) Int. Cl.
*A61F 2/16*    (2006.01)
*A61F 9/007*    (2006.01)
*A61F 2/14*    (2006.01)

(52) U.S. Cl.
CPC ................ *A61F 2/161* (2015.04); *A61F 2/15* (2015.04); *A61F 9/007* (2013.01); *A61F 2002/1686* (2013.01); *A61F 2002/16903* (2015.04); *A61F 2002/169053* (2015.04)

(58) Field of Classification Search
CPC .... A61F 2/16; A61F 2/15; A61F 2/161; A61F 9/007; A61F 2002/169053; A61F 2002/16903; A61F 2002/1682; A61F 2002/1683; A61F 2002/1686; A61F 2002/16902; A61F 2002/16905
See application file for complete search history.

(56) References Cited

U.S. PATENT DOCUMENTS

| 4,666,444 | A | * | 5/1987 | Pannu | ........................ | A61F 2/16 |
| | | | | | | 623/6.45 |
| 6,013,101 | A | * | 1/2000 | Israel | ..................... | A61F 2/1629 |
| | | | | | | 623/6.43 |
| 2008/0154362 | A1 | * | 6/2008 | Cumming | ............. | A61F 2/1629 |
| | | | | | | 623/6.37 |

* cited by examiner

*Primary Examiner* — David H Willse
*Assistant Examiner* — Tiffany P Shipmon
(74) *Attorney, Agent, or Firm* — North Shore Patents, P.C.; Michele Liu Baillie

(57) ABSTRACT

The present disclosure relates to a posterior chamber intraocular lens with swivel haptics for capsulotomy fixation in an eye. The posterior chamber intraocular lens includes a circular optic and at least one pair of swivel haptics. The circular optic is configured to be positioned within a capsular bag of the eye. The circular optic includes plurality of positioning holes on a periphery. The at least one pair of swivel haptics is positioned on the circular optic. The at least one pair of swivel haptics is configured to be rotated away from the circular optic and fixed above an anterior capsule of the eye.

12 Claims, 4 Drawing Sheets

POSTERIOR CHAMBER INTRAOCULAR LENS WITH SWIVEL HAPTICS FOR CAPSULOTOMY FIXATION

FIELD OF THE INVENTION

The present disclosure generally relates to intraocular lenses and more particularly to a posterior chamber intraocular lens using swivel haptics for capsulotomy fixation in an eye.

BACKGROUND TO THE INVENTION

Modern cataract surgeries are typically followed by implantation of an intraocular lens (IOL) in an eye to enable spectacle free vision post operation. The IOL can be implanted in either an anterior chamber or posterior chamber of the eye. The IOL is required to be of a flexible and foldable material such that an eye surgeon can easily inject the IOL through a small incision into a capsular bag of the eye and further correctly position the IOL. The IOL typically includes an optic with one or more haptics or elements that support the optic.

Position of the IOL, however, cannot be accurately determine pre-operatively. Hence, effective lens position of the IOL is not attained and accounts for around 0.75 diopter (D) error. Moreover, the IOL can move out of position (also referred to decentration) thereby creating loss in effective vision and user dissatisfaction. Some examples of IOLs that have been designed to overcome the above problems are discussed in detail below.

In one example, the IOL, a hydrophilic acrylic IOL, includes a 5 millimeter (mm) optic surrounded by a peripheral groove that is defined by elliptical haptics. The elliptical haptics are perpendicularly oriented to each other and allow for accommodation of both anterior and posterior capsulorrhexis (a continuous circular tear in anterior and posterior capsule, respectively). However, in this example, the eye surgeon should create perfectly sized anterior and posterior capsulorrhexis (slightly lesser than the 5 mm optic) which is a challenging process. Moreover, there is a possibility of stretching the capsular bag, during positioning of the IOL, leading to tearing of the capsular bag. In such cases, the IOL has to be explanted and not implanted.

Postoperative follow-ups of the hydrophilic acrylic IOL have determined non-occurrence of posterior capsule opacification (PCO) and visual axis reproliferation (VAR). Centration stability of the hydrophilic acrylic IOL is also determined to be stable over time. Hence, despite the centration stability and the non-occurrence of the PCO that enable accommodation of complex IOLs, for example Toric IOLs and multifocal IOLs, alignment of the hydrophilic acrylic IOL is still incorrect.

In another example, the IOL, an anti-dysphotopic IOL, includes a grove on an anterior edge near around periphery of the optic. Capsulotomy can be captured in the groove and bulk of the IOL is placed in the capsular bag. However, there are chances that the capsulotomy is not captured. The IOL is also larger in size and requires a wider incision for implantation. Further, haptics in the IOL are thick and are in contact with back of iris of the eye, thereby causing iris chaffing and pigment dispersion over time.

The anti-dysphotopic IOL is used to prevent negative dysphotopsia after cataract surgery. The anti-dysphotopic IOL further provides centration stability due to use of a flange of the anterior edge that overrides anterior capsulotomy. However, the anti-dysphotopic IOL is not successful for prolonged use.

Hence, the IOLs currently in use typically face issues such as difficulty in removal of an ophthalmic viscosurgical device (OVD) from behind the eye, complicated designs and technical difficulty, need of special instruments and injectors, capsulotomy tears, capsular block, the iris chaffing, and the pigment dispersion.

SUMMARY OF THE INVENTION

This summary is provided to introduce a selection of concepts in a simplified format that are further described in the detailed description of the invention. This summary is not intended to identify key or essential inventive concepts of the subject matter, nor is it intended for determining the scope of the invention.

An example of a posterior chamber intraocular lens for capsulotomy fixation in an eye includes a circular optic and at least one pair of swivel haptics. The circular optic is configured to be positioned with in a capsular bag of the eye. The circular optic includes plurality of positioning holes on a periphery. The at least one pair of swivel haptics is positioned on the circular optic. The at least one pair of swivel haptics is configured to be rotated away from the circular optic and fixed above an anterior capsule of the eye.

An example of a posterior chamber intraocular lens for capsulotomy fixation in an eye includes a circular optic, a pair of curved haptics, a pair of pivots, and a pair of swivel haptics. The circular optic is configured to be positioned within a capsular bag of the eye and includes a plurality of positioning holes on a periphery. A first positioning hole of the plurality of positioning holes is at a right end of the circular optic. A second positioning hole of the plurality of positioning holes is at a left end of the circular optic. The pair of curved haptics extends from the circular optic in diagonally opposed directions to each other. A first curved haptic of the pair of curved haptics extends from a top end of the circular optic to rest against a top inner periphery of the capsular bag. A second curved haptic of the pair of curved haptics extends from in a bottom end of the circular optic to rest against a bottom inner periphery of the capsular bag. A first pivot of the pair of pivots is positioned the first positioning hole and a second pivot of the pair of pivots positioned in the second positioning hole. The pair of swivel haptics in positioned perpendicular to the pair of curved haptics. A first swivel haptic of the pair of swivel haptics is configured to swivel on the first pivot and a second swivel haptic of the pair of swivel haptics is configured to swivel on the second pivot. The first swivel haptic and the second swivel haptic are configured to be rotated away from the circular optic and fixed into an angular position above an anterior capsule of the eye.

To further clarify advantages and features of the present invention, a more particular description of the invention will be rendered by reference to specific embodiments thereof, which is illustrated in the appended figures. It is appreciated that these figures depict only typical embodiments of the invention and are therefore not to be considered limiting of its scope. The invention will be described and explained with additional specificity and detail with the accompanying figures.

BRIEF DESCRIPTION OF THE FIGURES

The invention will be described and explained with additional specificity and detail with the accompanying figures in which.

Further, skilled artisans will appreciate that elements in the figures are illustrated for simplicity and may not have been necessarily been drawn to scale. Furthermore, in terms of the construction of the device, one or more components of the device may have been represented in the figures by conventional symbols, and the figures may show only those specific details that are pertinent to understanding the embodiments of the present invention so as not to obscure the figures with details that will be readily apparent to those of ordinary skill in the art having benefit of the description herein.

DESCRIPTION OF THE INVENTION

For the purpose of promoting an understanding of the principles of the invention, reference will now be made to the embodiment illustrated in the figures and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are exemplary and explanatory of the invention and are not intended to be restrictive thereof.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional component. Appearances of the phrase "in an embodiment", "in another embodiment" and similar language throughout this specification may, but do not necessarily, all refer to the same embodiment.

Unless otherwise defined, all technical and scientific terms used herein have the same meaning as commonly understood by one of ordinary skill in the art to which this invention belongs. The system, methods, and examples provided herein are illustrative only and not intended to be limiting.

Embodiments of the present invention will be described below in detail with reference to the accompanying figures.

Figure 1:
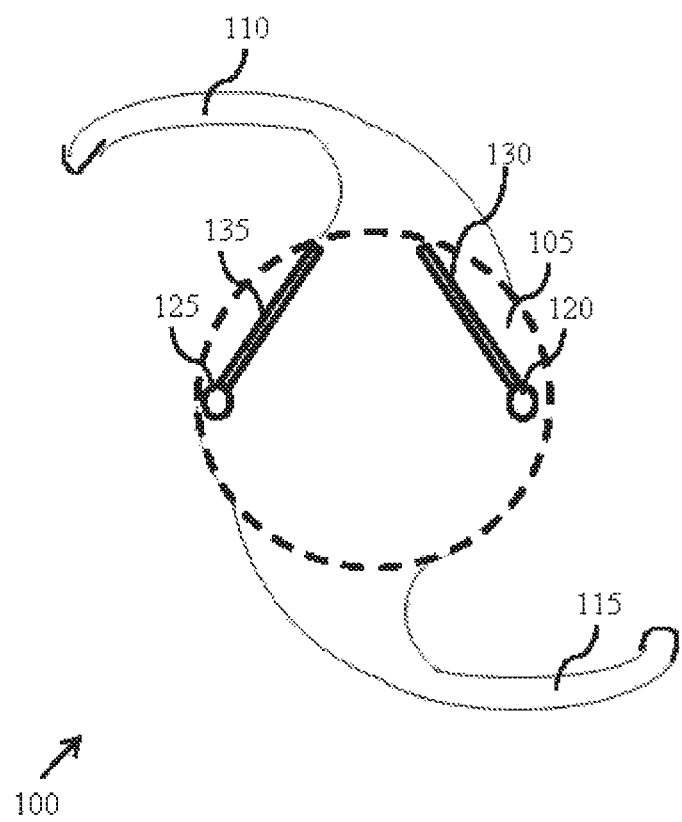
FIG. 1 illustrates a front view of a posterior chamber intraocular lens, in accordance with an embodiment.

FIG. 1 illustrates a front view of a posterior chamber intraocular lens 100, in accordance with an embodiment. Herein, the 'posterior chamber intraocular lens (IOL)' 100 refers to a synthetic artificial lens that is implanted inside a posterior chamber of an eye to replace focusing power of a natural lens that has been surgically removed, typically during cataract surgery. Hereinafter, the posterior chamber IOL 100 is referred to as the IOL 100. In an example, the IOL 100 is a pseudophakic IOL that completely replaces the natural lens of the eye. In an example, the IOL 100 is fixed in an anterior capsule of the capsular bag. In another example, the IOL 100 is fixed in a posterior capsule of the capsular bag. The IOL 100 can be implanted using a standard injector in, for example, a 2.8 millimeter (mm) incision in the capsular bag.

The IOL 100 is configured to focus light that comes into the eye through a cornea and a pupil onto a retina of the eye. The IOL 100 can be a hydrophilic acrylic IOL. Herein, the 'hydrophilic acrylic IOL' refers to an IOL that is made out of a flexible and foldable material referred to as hydrophilic acrylic. In some embodiments, the IOL 100 can be a hydrophobic acrylic IOL or a hydrophobic silicone IOL. The IOL 100 is configured for the eye as per appropriate prescription to provide effective vision for a user.

The IOL 100 can include one of an open loop intraocular lens, a closed loop intraocular lens, and a plate intraocular lens. The present disclosure is explained using an open loop intraocular lens including a pair of curved haptics. However, it should be noted that the IOL 100 can include the closed loop intraocular lens, the plate intraocular lens, and the like, and is not limited to the open loop intraocular lens.

The IOL 100 includes a circular optic 105, a pair of curved haptics, a pair of pivots, and a pair of swivel haptics. In an example, the IOL 100 includes the circular optic 105 (an aspheric optic) having a diameter of 6 millimeters (mm), a 360 degree square edge, and an overall diameter of 13 mm. The pair of curved haptics include a first curved haptic 110 and a second curved haptic 115. The pair of pivots include a first pivot 120 and a second pivot 125. The pair of swivel haptics include a first swivel haptic 130 and a second swivel haptic 135. It should be noted that the IOL 100 can include multiple pairs of swivel haptics other than the first swivel haptic 130 and the second swivel haptic 135. Further, the multiple pairs of swivel haptics swivel on corresponding pairs of pivots other than the first pivot 120 and the second pivot 125. The circular optic 105 is circular in shape and includes a plurality of positioning holes (not shown) on a periphery of the circular optic 105. The positioning holes include a first positioning hole and a second positioning hole. The first positioning hole is located at a right end of the circular optic 105 and the second positioning hole is located at a left end of the circular optic 105.

The first curved haptic 110 and the second curved haptic 115 extend outward from the circular optic 105 in diagonally opposed directions to each other. The first curved haptic 110 extends from a top end of the circular optic 105 and the second curved haptic extends from a bottom end of the circular optic 105. When injected into the capsular bag of the eye, the first curved haptic 110 is configured to rest against a top inner periphery of the capsular bag and the second curved haptic 115 is configured to rest against a bottom inner periphery of the capsular bag. In an example, the first curved haptic 110 and the second curved haptic 115 are also made of the hydrophilic acrylic. The first curved haptic 110 and the second curved haptic 115 are hence easily foldable for injection into the capsular bag. In an example, the first curved haptic 110 and the second curved haptic 115 have ends that are rounded or rolled.

Figure 2:
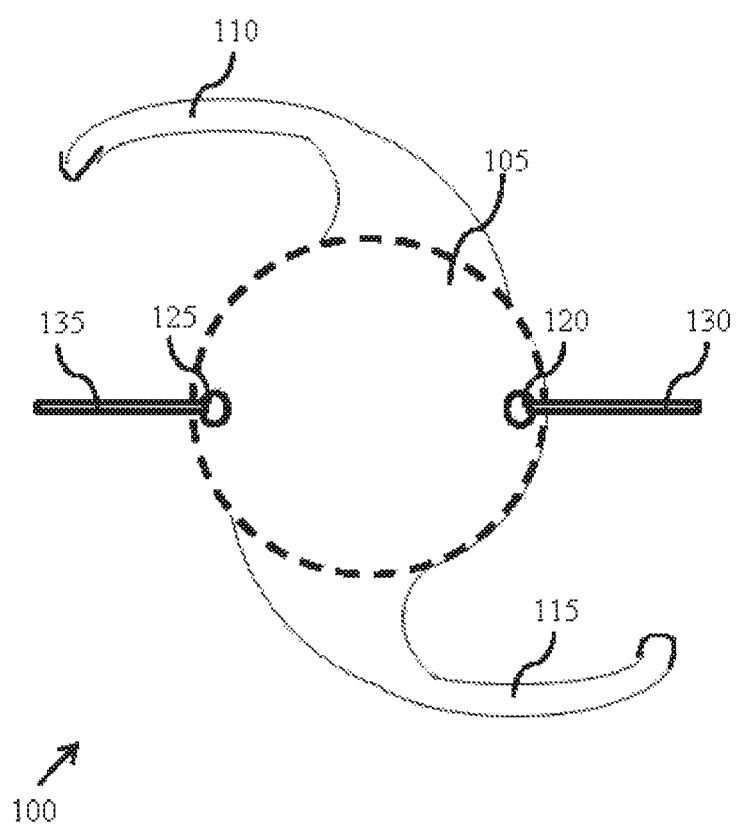
FIG. 2 illustrates a front view of a posterior chamber intraocular lens, in accordance with another embodiment.

The first pivot 120 is positioned in the first positioning hole at the right end of the circular optic 105. The second pivot 125 is positioned in the second positioning hole at the left end of the circular optic 105. The first swivel haptic 130 and the second swivel haptic 135 are positioned perpendicular to the pair of curved haptics. The first swivel haptic 130 is configured to swivel on the first pivot 120. The second swivel haptic 135 is configured to swivel on the second pivot 125. In an example, the first swivel haptic 130 is welded onto the first pivot 120 and the second swivel haptic 135 is welded onto the second pivot 125. The first swivel haptic 130 and the second swivel haptic 135 are configured to be rotated away from the circular optic and fixed into an angular position, for example a horizontal position, as illustrated in FIG. 2. In an example, the first swivel haptic 130 and the second swivel haptic 135 can rotate or swivel 360 degrees. In an example, the first swivel haptic 130 and the second swivel haptic 135 have ends that are rounded or tolled. In some embodiments, the first swivel haptic 130 and the second swivel haptic 135 can be used for multifocal and Toric platforms.

The first swivel haptic 130 and the second swivel haptic 135 are polymethyl methacrylate (PMMA) swivel haptics due to plastic memory capability PMMA. However, it should be noted that the first swivel haptic 130 and the second swivel haptic 135 can be made of another similar material and is not limited to PMMA. In some embodiments, the first swivel haptic 130 and the second swivel haptic 135 are each of 2.5 mm in length.

As illustrated in FIG. 1, the first swivel haptic 130 and the second swivel haptic 135 are in a closed position. For instance, in the closed position the first swivel haptic 130 and the second swivel haptic 135 are folded over the circular optic 105 before injecting the IOL 100 into the capsular bag. The first swivel haptic 130 and the second swivel haptic 135 continue to remain in the closed position in the capsular bag. An eye surgeon can use one or more devices to rotate the first swivel haptic 130 and the second swivel haptic 135 away from the circular optic 105. As illustrated in FIG. 2, the first swivel haptic 130 and the second swivel haptic 135 are rotated and fixed into the angular position in the capsular bag above the anterior capsule. Such fixation of the first swivel haptic 130 and the second swivel haptic 135 in the capsular bag over the anterior capsule enables stabilization, centration, and less tilt of the IOL 100.

In some embodiments, the IOL 100 can include a plurality of swivel haptics other than the first swivel haptic 130 and the second swivel haptic 135. Such swivel haptics can be diagonally located on the periphery of the circular optic 105 in corresponding positioning holes.

An example representation of the IOL 100 implanted in the capsular bag of the eye is explained with reference to FIG. 3. Another example representation of the IOL 100 implanted in the capsular bag of the eye is explained with reference to FIG. 4.

Figure 3:
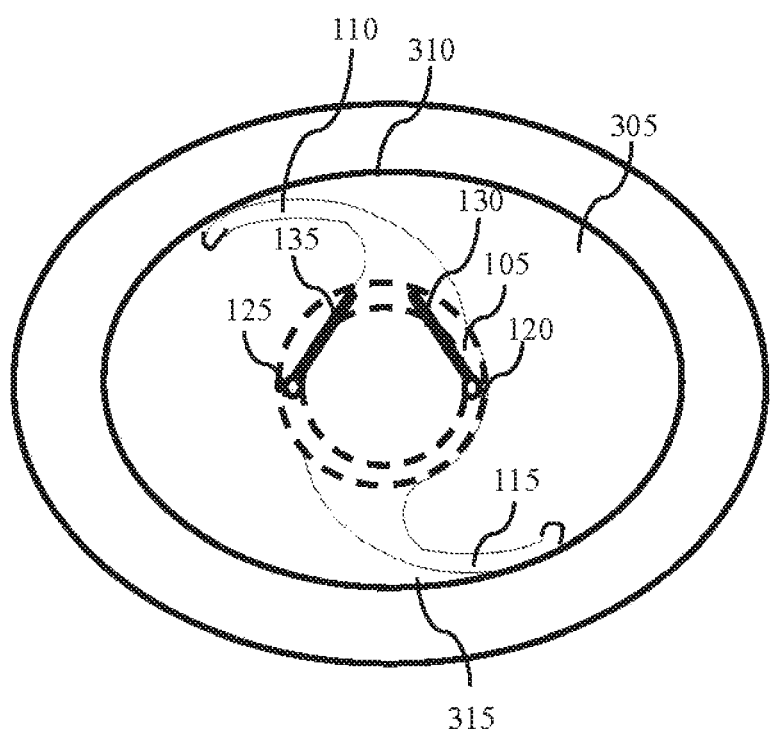
FIG. 3 illustrates a front view of a posterior chamber intraocular lens implanted in a capsular bag of an eye, in accordance with an embodiment.

Referring now to FIG. 3, a front view of the IOL 100 implanted in the capsular bag, for example the capsular bag 305, of the eye is illustrated. The IOL 100 is implanted by injection in the capsular bag 305 of the eye. The IOL 100 is in the closed position both before and immediately after the injection. The closed position of the IOL 100 includes the first swivel haptic 330 and the second swivel haptic 335 being folded over the circular optic 105. The first curved haptic 110 and the second curved haptic 115, once inserted into the capsular bag 305, adjust curvatures to rest against a top inner periphery 310 of the capsular bag 305 and a bottom inner periphery 315 of the capsular bag 305, respectively.

Figure 4:
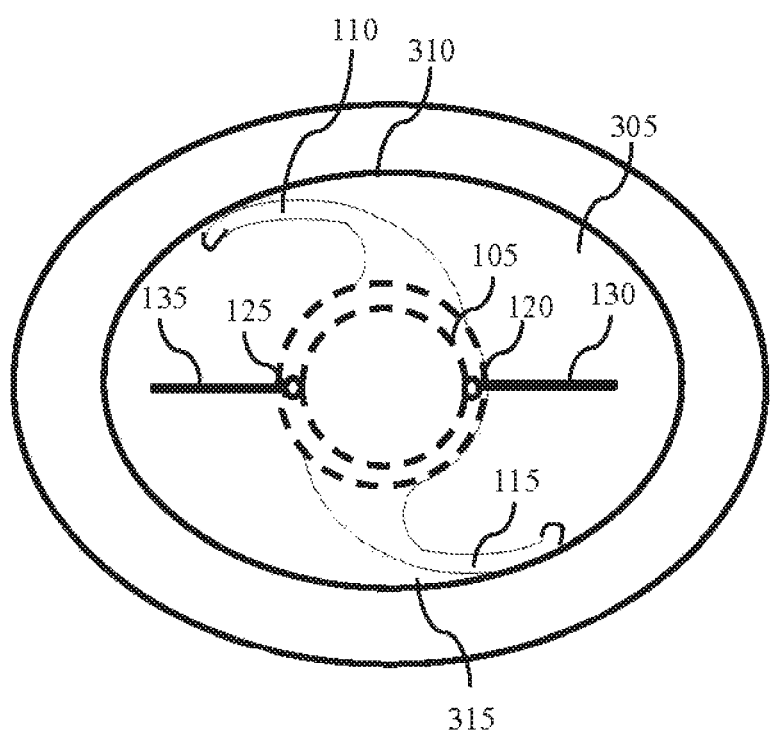
FIG. 4 illustrates a front view of a posterior chamber intraocular lens implanted in a capsular bag of an eye, in accordance with another embodiment.

Referring now to FIG. 4, a front view of the IOL 100 implanted in the capsular bag, for example the capsular bag 305, of the eye is illustrated, in accordance with another embodiment. The IOL 100 is implanted by injection in the capsular bag 305 of the eye in the closed position. The eye surgeon can now use the one or more devices to rotate the first swivel haptic 130 and the second swivel haptic 135 into the open position, for example into a horizontal position. The first swivel haptic 130 and the second swivel haptic 135 are rotated away from the circular optic 105 and are fixed into the horizontal position in the capsular bag 305 above the anterior capsule.

Various embodiments disclosed herein provide numerous advantages by providing a posterior chamber intraocular lens for capsulotomy fixation in an eye. The posterior chamber intraocular lens provided by the present disclosure is easy to use with a standard injector using, for example, a 2.8 millimeter (mm) incision in the capsular bag. The present disclosure does not require any special device or instruments or surgical training for implantation of the posterior chamber intraocular lens. The posterior chamber intraocular lens provide by the present disclosure can be used with both femtosecond laser-assisted cataract surgery (FLAC) and manual phacoemulsification as fixation is not dependent on capsulotomy size. The swivel haptics used in the posterior chamber intraocular lens ensure stable fixation of the posterior chamber intraocular lens and enables an effective lens position that is not influence by changes to the capsular bag. An anterior chamber depth measured in post-operative follow-ups is further determined to have no significant change on usage of the posterior chamber intraocular lens provided by the present disclosure.

Users of the posterior chamber intraocular lens in the present disclosure can experience a better postoperative refractive predictability. The present disclosure also allows the swivel haptics to provide rotational stability and centration stability (post-operative results) to intraocular lenses of Toric designs as well as to mono-focal and multi-focal lenses, irrespective of size of the capsular bag. The posterior chamber intraocular lens provided in the present disclosure further minimizes or prevents dysphotopsia (and especially prevents negative dysphotopsia) as a distance between a posterior iris plane and a lens plane is minimal. The posterior chamber intraocular lens further minimizes or prevents pigment dispersion due to use of thin PMMA swivel haptics, and allows easy explanation if required. The posterior chamber intraocular lens provided in the present disclosure also allows easy removal of viscoelastic from the capsular bag after implantation. The posterior chamber intraocular lens can be routinely used in cataract surgery with intraocular implants. The posterior chamber intraocular lens provided by the present disclosure has a simple design, is easy to manufacture and pack, is used with a standard injector, and has easy removal of the OVD from the capsular bag.

While specific language has been used to describe the disclosure, any limitations arising on account of the same are not intended. As would be apparent to a person in the art, various working modifications may be made to the method in order to implement the inventive concept as taught herein.

The figures and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

I claim:

1. A posterior chamber intraocular lens for capsulotomy fixation in an eye, the posterior chamber intraocular lens comprising:
   a circular optic configured to be positioned within a capsular bag of the eye, wherein the circular optic comprises a plurality of positioning holes on a periphery of the circular optic;
   at least one pair of pivots positioned at the plurality of positioning holes of the circular optic, wherein the at least one pair of pivots comprises a first pivot and a second pivot; and
   at least one pair of swivel haptics positioned on the circular optic, wherein a first swivel haptic of the at least one pair of swivel haptics is configured to swivel on the first pivot and a second swivel haptic of the at least one pair of swivel haptics configured to swivel on the second pivot, and wherein the at least one pair of swivel haptics is configured to be rotated away from the circular optic and fixed into an angular position above an anterior capsule of the eye.

2. The posterior chamber intraocular lens as claimed in claim 1, wherein the posterior chamber intraocular lens comprises one of an open loop intraocular lens, a closed loop intraocular lens, and a plate intraocular lens.

3. The posterior chamber intraocular lens as claimed in claim 1, wherein the plurality of positioning holes on the periphery of the circular optic comprises:
   a first positioning hole at a right end of the circular optic, the first positioning hole configured to receive the first pivot; and
   a second positioning hole at a left end of the circular optic, the second positioning hole configured to receive the second pivot.

4. The posterior chamber intraocular lens as claimed in claim 1, wherein the pair of swivel haptics are folded over the circular optic before injection into the capsular bag.

5. The posterior chamber intraocular lens as claimed in claim 1, wherein the posterior chamber intraocular lens is fixed in one of the anterior capsule and a posterior capsule of the capsular bag using the at least one pair of swivel haptics.

6. The posterior chamber intraocular lens as claimed in claim 1, wherein the posterior chamber intraocular lens comprises a hydrophilic acrylic intraocular lens or a hydrophobic acrylic intraocular lens.

7. The posterior chamber intraocular lens as claimed in claim 1, wherein the at least one pair of swivel haptics comprises either polymethyl methacrylate (PMMA) or other material swivel haptics.

8. A posterior chamber intraocular lens for capsulotomy fixation in an eye, the posterior chamber intraocular lens comprising:
   a circular optic configured to be positioned within a capsular bag of the eye, wherein the circular optic comprises a plurality of positioning holes on a periphery of the circular optic, a first positioning hole of the plurality of positioning holes at a right end of the circular optic, and a second positioning hole of the plurality of positioning holes at a left end of the circular optic;
   a pair of curved haptics extending from the circular optic in diagonally opposed directions to each other, a first curved haptic of the pair of curved haptics extending from a top end of the circular optic to rest against a top inner periphery of the capsular bag, and a second curved haptic of the pair of curved haptics extending from a bottom end of the circular optic to rest against a bottom inner periphery of the capsular bag;
   a pair of pivots, a first pivot of the pair of pivots positioned in the first positioning hole, and a second pivot of the pair of pivots positioned in the second positioning hole; and
   a pair of swivel haptics positioned perpendicular to the pair of curved haptics on the circular optic, a first swivel haptic of the pair of swivel haptics configured to swivel on the first pivot, a second swivel haptic of the pair of swivel haptics configured to swivel on the second pivot, the first swivel haptic and the second swivel haptic configured to be rotated away from the circular optic and fixed into an angular position above an anterior capsule of the eye.

9. The posterior chamber intraocular lens as claimed in claim 8, wherein the pair of swivel haptics are folded over the circular optic before injection into the capsular bag.

10. The posterior chamber intraocular lens as claimed in claim 8, wherein the posterior chamber intraocular lens is fixed in one of the anterior capsule and a posterior capsule of the capsular bag using the pair of swivel haptics.

11. The posterior chamber intraocular lens as claimed in claim 8, wherein the posterior chamber intraocular lens comprises a hydrophilic acrylic intraocular lens or a hydrophobic acrylic intraocular lens.

12. The posterior chamber intraocular lens as claimed in claim 8, wherein the pair of swivel haptics comprises either polymethyl methacrylate (PMMA) or other material swivel haptics.

* * * * *